United States Patent
Angeli et al.

(10) Patent No.: US 11,083,640 B2
(45) Date of Patent: Aug. 10, 2021

(54) MULTILAYER MATERIAL AND ABSORBENT SANITARY ARTICLE COMPRISING THE SAME

(71) Applicant: Pantex International S.p.A., Sulmona (IT)

(72) Inventors: Pietro Angeli, Sulmona (IT); Gianluigi Fornoni, Sulmona (IT); Carmine Di Benedetto, Sulmona (IT); Antonio Caira, Sulmona (IT)

(73) Assignee: PANTEX INTERNATIONAL SPA, Sulmona (IT)

( * ) Notice: Subject to any disclaimer, the term of this patent is extended or adjusted under 35 U.S.C. 154(b) by 751 days.

(21) Appl. No.: 15/302,952

(22) PCT Filed: Apr. 8, 2015

(86) PCT No.: PCT/IB2015/052561
§ 371 (c)(1),
(2) Date: Oct. 7, 2016

(87) PCT Pub. No.: WO2015/155716
PCT Pub. Date: Oct. 15, 2015

(65) Prior Publication Data
US 2017/0020748 A1    Jan. 26, 2017

(30) Foreign Application Priority Data
Apr. 8, 2014   (IT) .......................... TO2014A000300

(51) Int. Cl.
| | | |
|---|---|---|
| *A61F 13/512* | (2006.01) | |
| *A61F 13/511* | (2006.01) | |
| *A61L 15/42* | (2006.01) | |
| *A61L 15/24* | (2006.01) | |

(52) U.S. Cl.
CPC ...... *A61F 13/5123* (2013.01); *A61F 13/5116* (2013.01); *A61F 13/5126* (2013.01); *A61L 15/24* (2013.01); *A61L 15/425* (2013.01)

(58) Field of Classification Search
CPC .............. A61F 13/5123; A61F 13/5126; A61F 13/5116; A61L 15/24; A61L 15/425
See application file for complete search history.

(56) References Cited

U.S. PATENT DOCUMENTS

| | | | | |
|---|---|---|---|---|
| 4,173,046 A | * | 11/1979 | Gallagher | A61F 5/485 5/484 |
| 4,713,046 A | * | 12/1987 | Dupuy | B31B 50/66 493/6 |
| 5,895,380 A | * | 4/1999 | Turi | A61F 13/47218 604/383 |
| 5,924,134 A | * | 7/1999 | Taylor | A41D 31/085 2/81 |
| 2002/0164465 A1 | | 11/2002 | Curro | |
| 2010/0030170 A1 | * | 2/2010 | Keller | A61F 13/00017 604/360 |
| 2012/0244314 A1 | * | 9/2012 | Scheibner | B01D 67/0023 428/137 |
| 2015/0313763 A1 | * | 11/2015 | Bagger-Sjoback | A61F 13/4704 604/369 |

FOREIGN PATENT DOCUMENTS

| | | |
|---|---|---|
| DE | 19846857 | 3/2000 |
| WO | 00/28929 | 5/2000 |

OTHER PUBLICATIONS

European Patent Office, International Search Report, dated Jul. 24, 2015.
European Patent Office, Written Opinion of the International Searching Authority, dated Jul. 24, 2015.

* cited by examiner

*Primary Examiner* — Michele M Kidwell
(74) *Attorney, Agent, or Firm* — Leason Ellis LLP

(57) ABSTRACT

The invention describes a multilayer material comprising at least one first layer made of polymeric material having an upper face and a second layer made of closed cell foamed polymeric material having a lower face. The multilayer material comprises through holes which cross both the layers and occupy a surface of between 1 and 40% of the total surface of the upper face of said multilayer material. The multilayer material is advantageously used in an absorbent sanitary article in which the upper face of the first layer is positioned externally so that in use it is in contact with the user's skin and the lower face of the second layer is positioned towards the inside of the sanitary article in contact with other layers of polymeric material.

11 Claims, No Drawings

MULTILAYER MATERIAL AND ABSORBENT SANITARY ARTICLE COMPRISING THE SAME

CROSS-REFERENCE TO RELATED APPLICATIONS

The present application is a U.S. national stage of, and claims the priority benefit of, International Patent Application Serial No. PCT/IB2015/052561, filed Apr. 8, 2015 and Italian Patent Application Serial No. TO2014A000300, filed Apr. 8, 2014, the text and drawings of which are hereby incorporated by reference in their entireties.

TECHNICAL FIELD

The present invention concerns a multilayer polymeric material and an absorbent sanitary article comprising the same.

STATE OF THE ART

The development of absorbent sanitary articles and, in particular, of multilayer structures suitable for use in nappies or sanitary towels is the subject of intense commercial interest.

The materials of the present invention can also be used in all absorbent products such as, for example, disposable absorbent articles, sanitary towels, panty liners, interlabial devices, catamenial/medicinal/surgical tampons, nappies, incontinence pads, towels, medications, breastfeeding pads, underarm sweat guards, underwear products, trousers and shorts, make-up remover wipes, mattress/bed/chair protector pads, absorbent swabs for animals and similar. Below, by absorbent sanitary article we mean any one of the above-mentioned products.

Originally absorbent products were made of composite materials formed of a plurality of layers containing fabrics or fibres generally made of cotton which allowed body fluids to be absorbed.

Subsequently the structures were developed, incorporating cellulose pulp which is able to absorb 5-6 times its weight. Nowadays, for example, the structures of sanitary articles and, in particular, of nappies, sanitary towels and incontinence pads incorporate absorbent materials in gel such as polyacrylates in combination with cellulose fibres, for example, thus making it possible to market relatively fine multilayer structures.

Absorbent sanitary articles like children's nappies, sanitary towels or incontinence pads are typical applications.

For these purposes multilayer materials are used comprising a first layer in contact with the user's skin and called generally and herebelow topsheet, generally made of non-woven fabric. Below the topsheet, a further layer is optionally arranged adapted to acquisition and distribution of the liquid, followed by a layer of absorbent material and lastly a backsheet which must be waterproof.

The topsheet must be rapidly crossed by the liquids, but at the same time it must act as a barrier and avoid return of the liquids from the absorbent layer towards the user's skin, in particular it must avoid the surface in contact with the skin becoming wet and must maintain the feeling of dryness on the skin.

The more permeable the material composing the topsheet, the more efficiently it will allow liquids to pass through.

Furthermore the topsheet is often required to be soft to the touch, since it is in contact with the user's skin, and also give the user a feeling of cushioning. It is furthermore desirable for the topsheet to have a resilience to dry and wet in all directions.

The thicker the layer of material, the more difficult it is for the liquid to permeate.

Said problem has been solved by perforating the topsheet to allow the liquids to pass through the layer and rapidly reach the liquid acquisition and distribution layer and the absorbent material below.

However, perforation of the topsheet to accelerate the passage of the liquids is obtained by crushing the layer of material forming the topsheet, reducing the thickness thereof and therefore reducing the softness of the topsheet.

To attempt to solve this problem, topsheets have been used consisting of special composite materials or different perforation methods have been used.

Today the layers of materials constituting the topsheet are perforated via different methods:

a first method is needle perforation. In this method the film or strip of material that will constitute the topsheet is passed between two counter-rotating cylinders, the first of which is provided with needles arranged perpendicular to the surface of the cylinder and the second cylinder is provided with cavities in the surface complementary to the needles and adapted to house the needles when the cylinders rotate.

A second type of perforation, also called vacuum perforation, occurs when a hot film or strip of very thin material is made to rotate on a roller having a surface which is microperforated and depressurised on the inside. Due to the pressure difference between the inside and the outside of the roller, the film or strip is subject to microperforations.

A third type of perforation is also called perforation by abrasion and is described, for example, in the patent U.S. Pat. No. 3,408,776.

A fourth type of perforation is obtained with a method described, for example, in the patent EP0596970 and consists of two rotating counter-rollers, one of which is smooth and the other provided with protrusions maintained in contact with each other and having different peripheral speeds, in particular the smooth cylinder has a lower speed than the cylinder with protrusions so that when the strip of material passes on the contact line between the two cylinders, the protrusions make holes in the strip due to the speed differential.

Generally the topsheets are made of non-woven fabric. The thickness of the non-woven fabric layers depends on the technology with which they are produced. In any case the increase in thickness is closely connected with the increase in weight per square metre of material, which also generally entails a significant increase in costs.

Very thick materials produced with the so-called "air through bonded" technology, abbreviated to ATB, are frequently used as topsheets. The fibres that compose the strip of non-woven material are thermally bonded with a jet of hot air without contact with pressure cylinders, unlike what occurs with the commonest carded thermal bonded materials.

In addition to being very expensive, the ATBs do not ensure a sufficient cushioning effect, which is ideal for topsheets.

The commonest non-woven fabrics used as topsheets, although inexpensive, are no longer considered soft enough to the touch and therefore users are in search of alternatives that are more pleasant to wear.

The need is therefore felt for a multilayer material that can be used as a topsheet for absorbent sanitary articles, in particular for children's nappies, incontinence pads or sanitary towels, able to solve the above-mentioned problems and which can also be produced at a lower cost.

SUMMARY OF THE INVENTION

The object of the invention is therefore a multilayer material which is both soft, pleasant in contact with the skin and allows rapid passage of body fluids, but at the same time remains dry and can therefore be used as a topsheet for an absorbent sanitary article and has a resilience to dry and wet in all directions.

A second object of the present invention is an absorbent sanitary article, in particular a nappy, an incontinence pad or a sanitary towel comprising the above-mentioned multilayer material.

According to the present invention, the first object is achieved by a multilayer material according to claim 1.

According to the present invention, the second object is achieved by an absorbent sanitary article according to claim 15.

DISCLOSURE OF THE INVENTION

In the context of the present invention, by layer we mean a mass of homogeneous material laid more or less uniformly over a surface.

In the context of the present invention, by multilayer material we mean a material consisting of at least two distinct layers which are joined either by means of physical methods such as pressure or by means of chemical bonding agents like an adhesive, for example.

In the context of the present invention, by foam or foamed material we mean a material transformed via a process of chemical or physical expansion.

In the context of the present invention by closed cell foamed material we mean a material consisting of "closed microcells", which make it impermeable to water, resilient, with good resistance to compression. Closed cell foamed material differs from open cell foamed material due to the fact that the cells are spaced and each one is completely surrounded by solid material. Vice versa in an open cell material there is a passage of fluid between one cell and another, and therefore open cell material is not fluid-tight. It should be noted that a closed cell material is hydrophobic and waterproof.

According to the present invention it is advantageous to use a multilayer material as a topsheet for an absorbent sanitary article.

Preferably the multilayer material comprises at least two layers: a first outer layer to be used with one face in contact with the user's skin and a second inner layer with one face in contact in use with other materials.

In one aspect of the present invention, the first outer layer is formed of a layer of polymeric material soft to the touch, in particular and preferably, for example, at least one non-woven fabric or at least one microperforated film and/or both, or another material adapted to provide a feeling of softness.

The first outer layer can also be formed of several layers such as two non-woven fabrics combined together or also a non-woven fabric combined with a microperforated film or two microperforated films.

The first outer layer comprises an upper face which in use will be in contact with the user's skin.

The first layer is more preferably a material chosen from the group consisting of a non-woven fabric and/or a microperforated film.

The non-woven fabric is preferably polyethylene- or polypropylene-based or also bicomponent.

If it is bicomponent, the non-woven fabric preferably comprises fibres in two concentric layers in which the central one can be polypropylene or polyester while the outer layer can be polyethylene or polypropylene or polyester copolymer.

The non-woven fabric is preferably thermally bonded and more preferably has a weight of between 5 and 30 g per square metre. The thickness is preferably between 0.05 and 0.7 mm.

The MD tensile strength is preferably between 10 and 50 N/50 mm and the MD elongation at break between 10 and 70%.

MD is the Machine Direction, i.e. the direction of forward movement of the machine during production of the material, while CD is the Cross Direction, or direction transverse to the former.

The microperforated films preferably have a number of holes per $cm^2$ between 300 and 1000 preferably with mean area of each hole less than 0.1 $mm^2$, more preferably less than 0.05 $mm^2$.

Preferably the area occupied by the holes is between 8 and 20%.

The area occupied by the holes, also called open area, is measured on the free film and not on the multilayer material according to the present invention when the microperforated film has already been combined with other materials since the microholes no longer pass through the multilayer.

Measurement of the area of the holes is always taken on the upper face of the film which in use will be in contact with the user's skin.

Preferably the microperforated film is arranged with the cones formed by the perforations facing in use towards the user. Said configuration is the one that provides the effect of softness.

The microperforation of the first layer can be obtained preferably by vacuum process or by calendering.

The latter process is described for example in the patent IT1360702.

According to said patent, the films are preferably microperforated by means of a method for forming a polymeric material in tape, film, membrane or layer form comprising a stage of passing the polymeric material between a first smooth cylinder and a second cylinder provided with pointed tips on the outer surface adapted to create deformations which extend from a first face of the polymeric material, thus allowing a polymeric material to be obtained with a tactile sensation similar to fabric or silk or non-woven fabric. The first and the second cylinder are pressurised against each other, the first cylinder provided with pointed tips is rotated at a peripheral speed greater than the peripheral speed of the second smooth cylinder with a consequent reciprocal sliding action between the surfaces of the cylinders. The number of pointed tips of the first cylinder is greater than 100 per $cm^2$ of surface of the cylinder, preferably the number of pointed tips of the first cylinder is between 300 per $cm^2$ and 1000 per $cm^2$ of cylinder surface.

For example, in a first step of formation of deformations, the linear pressure between the cylinders is 90 N/mm respectively and the sliding or friction percentage is 50%. The temperature of the cylinder with the pointed tips can be 85° C., for example, and the temperature of the smooth cylinder 75° C. Table 1 shows some examples of polymeric materials obtained from cylinders having pointed tips with frustoconical shape and elliptical base which can be used to form a polymeric material for use as a first layer according to one aspect of the present invention.

TABLE 1

|  | Cylinder 1 | Cylinder 2 | Cylinder 3 |
|---|---|---|---|
| No. of holes (cm$^2$) | 430 | 223 | 531 |
| % surface area occupied by holes | 21.9% | 16.3% | 27.1% |
| Area of hole base | 0.051 | 0.073 | 0.051 |
| Shape of hole base | elliptical | elliptical | elliptical |
| Pointed tip base dimensions | 0.26 mm × 0.25 mm | 0.31 mm × 0.30 mm | 0.26 mm × 0.25 mm |
| Height | 0.3 mm | 0.4 mm | 0.2 mm |
| Angle of sides | 15° | 20° | 15° |
| Machine direction pitch | 0.89 mm | 1.24 | 0.81 |
| Transverse pitch | 0.52 mm | 0.72 mm | 0.47 mm |

The microperforated films obtained have a tactile effect similar to silk in the layer which in use comes into contact with the skin.

In one aspect of the present invention, the multilayer further comprises at least one second layer made of a closed cell foamed polymeric material.

The second layer of the multilayer material of the present invention preferably comprises a polyolefin, more preferably comprises a material chosen from the group consisting of polyethylene, polypropylene or mixtures thereof, even more preferably it comprises polyethylene.

Preferably the second layer is made of polyethylene, even more preferably it is made of low density polyethylene.

Optionally the second layer can be formed of several layers of closed cell foamed material combined together.

Even more preferably, the closed cell foamed material is in the form of film, tape or sheet.

Preferably the foamed material can be coloured or white to differentiate its appearance.

Even more preferably, the closed cell foamed material has a thickness of between 0.2 and 3 mm, more preferably between 0.6 and 2 mm, even more preferably between 0.8 and 1.5 mm.

Preferably the closed cell foamed material has a density between 5 and 60 Kg/m$^3$, more preferably between 10 and 40 Kg/m$^3$.

The characteristics of some closed cell foamed materials made of polyethylene that can be used in the present invention are given in table 2.

TABLE 2

|  | Unit | Cell-Aire 0.8 mm | Cell-Aire 1.0 mm | Cell-Aire 1.5 mm |
|---|---|---|---|---|
| Base weight | g/m$^2$ | 13.9 | 17.7 | 19.5 |
| Thickness | Mm | 0.83 | 1.3 | 1.55 |
| Density | Kg/m$^3$ | 16.7 | 13.6 | 12.6 |

Preferably the foamed material can be perforated before being coupled to other materials.

In one aspect of the present invention, both the first and the second layer of the multilayer material are perforated with through holes.

If the foamed material has already been perforated, the new holes can correspond to the old holes of the foamed material or they can be separate, but in any case they must be through holes.

Preferably the holes occupy a surface of between 1 and 50% of the total surface. The surface occupied by the holes or "open area" is calculated on the upper face of the first layer which in use will be in contact with the user.

More preferably, the holes occupy a surface of between 1 and 40%, even more preferably between 10 and 30%.

It is clear that further layers such as, for example, a further layer of non-woven fabric below the closed cell foamed material can be combined with the multilayer of the present invention.

It should be underlined that whatever work method is used for making the holes, it cannot ensure that all the holes are perfectly identical in terms of shape and dimensions and that there is always the same number of holes per unit of measurement and neither that the holes extend uniformly over the surface. However, how to calculate both the surface occupied by the holes per unit of measurement, also known as open area, and the number and dimensions of the single holes obtained as a mean of different measurements, at least 3 measurements, is known in the sector.

The mean area of the single holes is preferably between 0.05 and 1 cm$^2$, more preferably between 0.1 and 0.8 cm$^2$.

The number of holes per cm$^2$ is preferably between 1 and 40 cm$^2$, more preferably between 5 and 30 per cm$^2$.

The multilayer material preferably has a combination of parameters of those previously reported and in particular a surface occupied by the holes between 1 and 10% and a mean area of the holes between 0.1 and 1 cm$^2$ and a number of holes per cm$^2$ between 5 and 25; or a surface occupied by the holes between 1 and 10% and a mean area of the holes between 0.05 and 0.3 cm$^2$ and a number of holes between 15 and 25; or a surface occupied by the holes between 10 and 20% and a mean area of the holes between 0.1 and 1 cm$^2$ and a number of holes between 15 and 25 cm$^2$.

The perforations can have different patterns and also be discontinuous and the discontinuities can be in CD or MD or be obtained with any one of the methods described previously. Preferred perforations are those described in the patent EP0596970.

The multilayer according to the present invention has proved particularly effective when used as topsheet in an absorbent sanitary article.

In particular, in this case below the multilayer material a layer adapted to acquisition and distribution of the liquid will preferably be arranged, then a layer of absorbent material is arranged and lastly a backsheet which must be waterproof. It is clear that there are numerous variations of absorbent sanitary articles, for example the layer adapted to acquisition and distribution of the liquid and the absorbent layer may consist of one single material or, vice versa, they may consist of 3 or more layers.

It is also possible to arrange below the layer of closed cell foamed material of the present invention a further layer of non-woven fabric to further increase the cushion effect and it is also possible not to use a layer for distribution of the fluid.

From an examination of the characteristics of the multilayer material produced according to the present invention, the advantages it provides are clear.

It has been experimentally verified that when the multilayer material of the present invention is used in an absorbent sanitary article and the through holes occupy an area of between 5 and 40%, the body fluids rapidly cross the multilayer material without wetting the latter due to the hydrophobicity of the layer of closed cell foamed material and partly also due to the hydrophobicity of the first layer in contact with the skin, thus resulting in a drier product with greater masking (non visibility) of the fluids on the surface and therefore greater user comfort.

Thanks to the presence of the through holes, the fluids can flow through without leaving a wet effect on the surface of the multilayer material which, in use, is in contact with the skin and without reducing the effect of softness and three-dimensionality.

It is also possible to use a first hydrophilic layer to obtain better run-off of the liquids on the surface.

The multilayer material according to the present invention will be described below also by means of examples without limiting the invention to them.

EXAMPLE 1

A multilayer material is formed consisting of a first layer made of a non-woven fabric coupled with a second layer of closed cell foamed polyethylene.

The first layer is a thermally bonded non-woven fabric with nominal weight of 13 g per square metre with the characteristics given in table 3:

TABLE 3

| Characteristics | Test method | Unit of measurement | Batch mean |
|---|---|---|---|
| Thickness | WSP 120.6 | mm | 0.18 |
| MD tensile strength | WSP 110.4 | N/50 mm | 20.11 |
| MD elongation | WSP 110.4 | % | 16.05 |
| CD tensile strength | WSP 110.4 | N/50 mm | 3.21 |

The second layer is a closed cell foamed polyethylene with thickness of 1 mm. In this case a known material such as Cell-Aire was used. Said material has an elongation at break of 8.5 mm, a punching test resistance of 5.5 N according to standard SAC-PL 012, longitudinal tensile strength of 10.9 N and transverse tensile strength of 4 N according to standard DIN 53571, longitudinal elongation at break of 19.9% and transverse elongation at break of 34% according to standard DIN53571.

The laminate composed of the above two layers is perforated by needle technology with two perforation patterns with 11 points/cm$^2$ and 18 points/cm$^2$.

The data relative to the perforation of the two laminates with 18 and 11 pins or points/cm$^2$ are given in tables 4 and 5:

TABLE 4

| 18 pins | Percentage area occupied by holes | Mean area of holes | No. holes/cm$^2$ | Diameter of holes mm |
|---|---|---|---|---|
| mean | 5.69 | 0.32 | 17.73 | 0.64 |

TABLE 5

| 11 pins | Percentage area occupied by holes | Mean area of holes | Number of holes/cm$^2$ | Diameter of holes mm |
|---|---|---|---|---|
| mean | 7.29 | 0.72 | 10.13 | 0.96 |

Since the perforation method does not ensure that there is always an exact quantity of holes in the unit of measurement, the mean must be obtained which is the result provided in the table. The number and dimensions of the holes in one cm$^2$ can actually be double or half the mean.

The first layer of non-woven fabric can be replaced by a microperforated film made of polyethylene formed of a microperforated material with 52 mesh in which the microperforations have been obtained by the vacuum method and using the same perforation pattern as shown in tables 4 and 5, for example having the characteristics given in table 6:

TABLE 6

| Characteristics | Test method | Unit of measurement | Batch mean |
|---|---|---|---|
| Base weight | WSP 130.1 | g/m$^2$ | 10.35 |
| Thickness | WSP 120.6 | Mm | 0.30 |
| MD tensile strength | ASTM D882 | N/inch | 5.04 |
| MD elongation | ASTM D882 | % | 145.74 |
| CD tensile strength | ASTM D882 | N/inch | 2.13 |
| CD elongation | ASTM D882 | % | 415.07 |
| Open Area PIN-OUT | | % | 13.97 |

EXAMPLE 2

To form a multilayer material, the materials used both for the first and for the second layer are the same as those given in example 1, but the perforation pattern is different.

In particular, to perform the perforation, in this case a "line" perforation pattern was used. In this case the multilayer material is obtained with a method according to which the material is perforated between two pressurised rollers on top of each other, the first roller having protrusions to perforate the material and the second roller rotating at a different speed from that of the first roller and with projecting parts with contact areas arranged to perforate the material together with the protrusions. The contact areas of the projecting parts are spaced by depressions to receive the processed material and have dimensions greater than the contact faces of the perforation projections. The perforation is made at the contact areas which leave an impression on the material. The contact areas are elongated and the length is at least four times the width so as to define a line or band. The line thus defined can be continuous or discontinuous in the machine direction. The main axis of the line can be either parallel or inclined with respect to the machine direction. The main axis of the line can follow a preferably periodic undulating path.

The pointed tips of a cylinder engraved with a pattern of approximately 80 points act preferably on the smooth part of the cylinder with channels. This results in the formation of a line of holes, no more than two of which are in cross direction.

Table 7 shows the characteristics of the holes for a line perforation example obtained with the method described above.

TABLE 7

| Line perforations | Percentage area occupied by holes | Mean area of holes | No. of holes/cm$^2$ | Diameter of holes mm |
|---|---|---|---|---|
| mean | 3.56 | 0.17 | 20.69 | 0.47 |

EXAMPLE 3

A multilayer material is formed comprising a first layer formed of a microperforated material with 52 mesh in which the microperforations have been obtained by the vacuum method and the characteristics of which can be found in table 3 of example 1 and a second layer comprising a closed cell foamed polyethylene, the characteristics of which are given in example 1.

In this case the perforation pattern allows elliptical holes to be obtained in the direction of the sliding of the film during the hole formation phase.

Table 8 shows the characteristics of the holes.

TABLE 8

| Undulating perforations | Percentage area occupied by holes | Mean area of holes | No. of holes/cm$^2$ | Diameter of holes mm |
|---|---|---|---|---|
| mean | 14.24 | 0.65 | 21.85 | 0.91 |

It should be noted that in this case the holes have an elliptical shape.

It is important to note that both the line perforation pattern in table 7 and the undulating perforation pattern in table 8 are continuous patterns in which the development on a cylinder will be helical.

The invention claimed is:

1. An absorbent sanitary article comprising a multilayer material, said multilayer material comprising at least one first layer made of polymeric material having an upper face and a second layer made of closed cell foamed polymeric material having a lower face, wherein said multilayer material comprises through holes which cross both the layers and occupy a surface of between 1 and 40% of a total surface of the upper face of said multilayer material, a mean area of each of said through holes calculated at a base of said through holes is between 0.05 and 0.5 cm' and a number of said through holes is between 1 and 40 per cm', said first layer made of polymeric material comprising a substance chosen from the group consisting of a non-woven fabric having a MD tensile strength of between 10 and 50 N/50 mm or a microperforated film with the through holes formed by microperforations and configured to, in use, face towards a user to provide an effect of softness and wherein said upper face of said first layer is positioned externally so that said upper face is configured to, in use, contact skin of the user and said lower face of said second layer is positioned towards an inside of said absorbent sanitary article in contact with other layers of polymeric material.

2. The absorbent sanitary article according to claim 1, characterised in that said through holes occupy a surface of between 5 and 30% of the total surface of the upper face of said multilayer material.

3. The absorbent sanitary article according to claim 1, characterised in that the number of said through holes is between 5 and 30 per cm$^2$.

4. The absorbent sanitary article according to claim 1, characterised in that:
the holes occupy a surface of between 1 and 10%, the mean area of the holes is between 0.1 and 1 cm$^2$ and the number of holes per cm$^2$ is between 5 and 25, or
the holes occupy a surface of between 1'1 and 10%, the mean area of the holes is between 0.05 and 0.3 cm$^2$ and the number of holes per cm$^2$ is between 5 and 25, or
the holes occupy a surface of between 10 and 20%, the mean area of the holes is between 0.1 and 1 cm$^2$ and the number of holes per cm$^2$ is between 5 and 25.

5. The absorbent sanitary article according to claim 1, characterised in that said second layer made of closed cell foamed polymeric material comprises a polyolefin.

6. The absorbent sanitary article according to claim 1, characterised in that said second layer made of closed cell foamed polymeric material is in polyethylene.

7. The absorbent sanitary article according to claim 1, characterised in that said second layer made of closed cell foamed polymeric material has a density of between 5 and 40 kg/m$^3$.

8. The absorbent sanitary article according to claim 1, characterised in that said second layer made of closed cell foamed polymeric material has a thickness of between 0.2 and 3 mm.

9. The absorbent sanitary article according to claim 1, characterised in that said microperforated film comprises a number of holes between 300 per cm$^2$ and 1000 per cm$^2$.

10. Absorbent sanitary article comprising a multilayer material, said multilayer material comprising at least one first layer made of polymeric material having an upper face and a second layer made of closed cell foamed polymeric material having a lower face, wherein said multilayer material comprises through holes which cross both the layers and occupy a surface of between 1 and 40% of a total surface of the upper face of said multilayer material, a mean area of each of said through holes calculated at a base of said through holes is between 0.05 and 0.5 cm$^2$ and a number of said through holes is between 1 and 40 per cm$^2$, said first layer made of polymeric material comprises a substance chosen from the group consisting of non-woven fabric or a microperforated film and wherein said upper face of said first layer is configured to be, in use, positioned externally so that said upper face is in contact with skin of a user and said lower face of said second layer is positioned towards an inside of said absorbent sanitary article in contact with other layers of polymeric material.

11. Multilayer material comprising at least one first layer made of polymeric material having an upper face and a second layer made of closed cell foamed polymeric material having a lower face, wherein said multilayer material comprises through holes which cross both the layers and occupy a surface of between 1 and 40% of a total surface of the upper face of said multilayer material, a mean area of each of said holes calculated at a base of said through holes is between 0.05 and 0.5 cm$^2$ and a number of said through holes is between 1 and 40 per cm$^2$, said first layer made of polymeric material comprises a substance chosen from the group consisting of non-woven fabric having a MD tensile strength of between 10 and 50 N/50 mm or a microperforated film with the through holes formed by the microperforations and configured, in use, face towards a user to provide an effect of softness.

* * * * *